US005714582A

United States Patent [19]

Wolfinbarger

[11] Patent Number: 5,714,582
[45] Date of Patent: Feb. 3, 1998

[54] INVERTEBRATE TYPE V TELOPEPTIDE COLLAGEN, METHODS OF MAKING, AND USE THEREOF

[75] Inventor: Lloyd Wolfinbarger, Norfolk, Va.

[73] Assignee: Bioscience Consultants, Norfolk, Va.

[21] Appl. No.: 405,979

[22] Filed: Mar. 17, 1995

[51] Int. Cl.$^6$ .............................. A61K 38/17; C07K 1/00; A23J 1/02

[52] U.S. Cl. .................. 530/356; 530/402; 530/418; 530/422; 530/427; 426/657

[58] Field of Search .................... 530/356, 402, 530/418, 422, 427, 857; 426/675; 623/1

[56] References Cited

U.S. PATENT DOCUMENTS

| | | | |
|---|---|---|---|
| 2,119,822 | 6/1938 | Mayehara | 99/15 |
| 2,920,000 | 1/1960 | Hochstadt et al. | 106/161 |
| 2,934,446 | 4/1960 | Highberger et al. | 106/155 |
| 2,934,447 | 4/1960 | Highberger et al. | 106/155 |
| 3,014,024 | 12/1961 | Lieberman et al. | 260/117 |
| 3,034,852 | 5/1962 | Nishihara | 18/54 |
| 3,121,049 | 2/1964 | Nishihara | 195/6 |
| 3,131,130 | 4/1964 | Oneson | 195/6 |
| 3,303,038 | 2/1967 | Klevens | 106/155 |
| 3,314,861 | 4/1967 | Fujii | 195/6 |
| 3,491,760 | 1/1970 | Braun et al. | 128/334 |
| 3,530,037 | 9/1970 | Nishihara | 195/6 |
| 3,562,820 | 2/1971 | Braun | 3/1 |
| 3,563,228 | 2/1971 | Seiderman | 128/1 |
| 3,632,350 | 1/1972 | Battista | 99/1 |
| 3,873,749 | 3/1975 | Carpenter et al. | 426/350 |
| 4,002,739 | 1/1977 | Turner et al. | 424/177 |
| 4,021,522 | 5/1977 | Daniel | 264/138 |
| 4,130,555 | 12/1978 | Ohtsuka et al. | 260/117 |
| 4,184,360 | 1/1980 | Vadnay et al. | 73/28 |
| 4,268,131 | 5/1981 | Miyata et al. | 351/160 H |
| 4,295,894 | 10/1981 | Cioca et al. | 106/155 |
| 4,350,629 | 9/1982 | Yannas et al. | 260/123.7 |
| 4,391,749 | 7/1983 | Engvall et al. | 260/123.7 |
| 4,407,829 | 10/1983 | Sjölander | 426/59 |
| 4,409,332 | 10/1983 | Jefferies et al. | 435/188 |
| 4,424,208 | 1/1984 | Wallace et al. | 424/177 |
| 4,451,397 | 5/1984 | Huc et al. | 260/123.7 |
| 4,488,911 | 12/1984 | Luck et al. | 106/161 |
| 4,505,817 | 3/1985 | Blomback et al. | 210/484 |
| 4,505,855 | 3/1985 | Bruns et al. | 260/123.7 |
| 4,557,764 | 12/1985 | Chu | 106/161 |
| 4,582,640 | 4/1986 | Smestad et al. | 260/123.7 |
| 4,600,533 | 7/1986 | Chu | 530/356 |
| 4,621,631 | 11/1986 | Pâques et al. | 128/156 |
| 4,642,117 | 2/1987 | Nguyen et al. | 623/11 |

(List continued on next page.)

OTHER PUBLICATIONS

Miura et al, *The Journal of Biological Chemistry*, vol. 260, No. 28, pp. 15352–15356, 1985.

Sato et al, *J. Agric. Food Chem.*, vol. 42, No. 3, pp. 675–676, 1994.

Sato et al. *J. Agric. Food Chem.*, vol. 39, No. 7, pp. 1222–1225, 1991.

Sato et al, *Journal of Food Science*, vol. 54, No. 6, pp. 1511–1514, 1989.

Kimura, S. et al., Collagen as the Major Edible Component of Jellyfish (*Stomolophus nomural*), *Journal of Food Science* 48:1758–1760 (1983).

Hsieh, P. et al., Potential of Utilizing Jellyfish as Food in Western Countries, *Trends in Food Science & Technology* 5(7):225–226 (1994).

Miura, S. et al., Jellyfish Mesogloea Collagen, *The Journal of Biological Chemistry* 260(28):15352–15356 (1985).

*Primary Examiner*—Cecilia J. Tsang
*Assistant Examiner*—Abdel A. Mohamed
*Attorney, Agent, or Firm*—Jones & Volentine, L.L.P.

[57] ABSTRACT

This invention relates to a method and process for the production of collagen preparations from marine invertebrates and compositions for these preparations. The collagen preparation includes telopeptide and atelopeptide fibrillar collagen of essentially invertebrate type V collagen. The collagen preparations may be used in a variety of medical, dental, cell culture, and food applications.

16 Claims, No Drawings

U.S. PATENT DOCUMENTS

| | | | |
|---|---|---|---|
| 4,655,980 | 4/1987 | Chu | 264/102 |
| 4,689,399 | 8/1987 | Chu | 530/356 |
| 4,703,108 | 10/1987 | Silver et al. | 530/356 |
| 4,725,671 | 2/1988 | Chu et al. | 530/356 |
| 4,789,663 | 12/1988 | Wallace et al. | 514/21 |
| 4,801,299 | 1/1989 | Brendel et al. | 623/1 |
| 4,803,075 | 2/1989 | Wallace et al. | 424/423 |
| 4,837,285 | 6/1989 | Berg et al. | 530/356 |
| 4,847,049 | 7/1989 | Yamamoto | 422/24 |
| 4,851,513 | 7/1989 | Devore et al. | 530/356 |
| 4,861,714 | 8/1989 | Dean, Jr. et al. | 435/68 |
| 4,863,856 | 9/1989 | Dean, Jr. et al. | 435/68 |
| 4,883,864 | 11/1989 | Scholz | 530/356 |
| 4,931,546 | 6/1990 | Tardy et al. | 530/356 |
| 4,980,403 | 12/1990 | Bateman et al. | 524/17 |
| 4,983,721 | 1/1991 | Davison | 530/356 |
| 5,024,841 | 6/1991 | Chu et al. | 424/422 |
| 5,035,896 | 7/1991 | Apfel et al. | 424/456 |
| 5,043,426 | 8/1991 | Goldstein | 530/356 |
| 5,093,474 | 3/1992 | Grossman et al. | 530/355 |
| 5,110,604 | 5/1992 | Chu et al. | 424/484 |
| 5,128,136 | 7/1992 | Bentley et al. | 424/443 |
| 5,138,030 | 8/1992 | Pachence | 530/356 |
| 5,162,506 | 11/1992 | Hadden | 530/412 |
| 5,219,576 | 6/1993 | Chu et al. | 424/484 |
| 5,231,169 | 7/1993 | Constantz et al. | 530/356 |
| 5,246,457 | 9/1993 | Piez et al. | 623/16 |
| 5,304,595 | 4/1994 | Rhee et al. | 525/54.1 |
| 5,316,942 | 5/1994 | Fink | 435/273 |
| 5,331,092 | 7/1994 | Huc et al. | 530/356 |
| 5,332,475 | 7/1994 | Mechanic | 204/157.68 |
| 5,344,917 | 9/1994 | Furukawa et al. | 530/356 |

INVERTEBRATE TYPE V TELOPEPTIDE COLLAGEN, METHODS OF MAKING, AND USE THEREOF

FIELD OF THE INVENTION

This invention relates to invertebrate type V collagen, methods of making collagen and methods for the use of these collagens. Collagen is a composition of proteins rich in glycine and proline arranged in a predominately alpha-helical structure which provides for a fibrillar structure which tends to form a gel in aqueous solution. These collagen preparations may be used in a variety of applications ranging from medical and dental to serving as a food source. The collagen possesses the attributes of being deliverable as a mixture in a fluidized state, as a mixture in a gel state, in a freeze-dried state, in a salt-precipitated state, or in a salt precipitated (salt-cured) dry state, of being compatible with tissues surrounding the site(s) of its application in medical and dental applications and of being digestible when used as a food-stuff. The process for the production of collagen from invertebrates including jellyfish, takes advantage of the physical and chemical characteristics of jellyfish where the jellyfish is essentially a gelatinous state of collagen in water surrounding simple digestive systems and attached to other collagenous structures generally described as tentitles which are used in the capture of prey for the purpose of feeding.

BACKGROUND OF THE INVENTION

The term jellyfish refers to hundreds of species of primitive marine animals belonging to the class Scyphozoa, phylum Coelenterata. Coelenterata is a phylum name derived from the Greek words meaning "hollow gut". It refers to important attributes of a group of invertebrate animals, called coelenterates, having a single internal cavity for digestion and excretion. Jellyfish often become abundant in coastal areas, particularly in late summer, and are regarded as a nuisance. Jellyfish sting swimmers, clog nuclear power plants, and fishing boat nets and, at times can cause severe damage to fishing nets owing to their huge volume and weight. In the water they are beautiful, colorful, and diaphanous creatures, yet most people only see them as a washed-up blob on the beach. Jellyfish can be found in both tropical and temperate waters of the world. The environmental factors affecting the occurrence of jellyfish are temperature, oxygen, salinity, and predation. Some species of jellyfish have great commercial potential. For example, the US coastal waters off the Florida Panhandle and all of the northern Gulf of Mexico provide an ideal environment for the seasonal proliferation of *Stomolophus meleagris,* which is commonly called the cannon-ball jellyfish. This species is found in abundance in certain areas of the world. For instance, it occurs from Southern New England, USA, to Venezuela and the Gulf of Mexico. One swarm observed at Port Arkansas, Tex., USA was estimated to have drifted through the channel at a rate of approximately 2 million per hour. Jellyfish occur world-wide, being caught in the Indian, Northwest Pacific and Western Central Pacific Oceans by Far Eastern countries including Thailand, Indonesia, Malaysia, the Philippines and China. In 1991, for example, the world harvest of jellyfish was 126,419 tons and Japanese buyers pay up to $25.00 per kilogram for large processed Grade "A" *Rholpilema esculenta* jellyfish.

Proteins belonging to the collagen group have been prepared from a variety of mammalian sources, including but not limited to, bovine, porcine, human, and chicken tissues, and have included a wide variety of types of proteins which have been used to categorize these proteins into classes variously defined as, including but not limited to, types I, II, III, V, VI, and X. The white connective tissues of vertebrate animals comprises a composite of protein fibers which are exceptionally strong and have only short range elasticity, and interfiber materials which are gel-like in nature. Connective tissue exists in the vertebrate animal body in a wet condition and has therefore evolved to show natural characteristics of wet strength. Prior to the present invention, the most readily available form of tissue derived collagen was from animal skin. In these skins the protein fibers constituted a dense three dimensional feltwork interconnected by interfiber material. Due to the extensive entanglement of the fibers with one another, workers in the art considered that the only way to break it apart was to sever it into microscopic particles as by colloid milling as described in U.S. Pat. No. 3,634,561 by Hawkins et al. Naturally occurring vertebrate connective tissue is used to form leather, sausage skins, and catgut however the irregular and variable shape of naturally occurring connective tissue is a serious disadvantage of the production of these products. Numerous workers in the art have sought a method of breaking down the fiber dispersion comprising treating of a collagenous material such as hide corium with a solution containing alkaline earth metal hydroxide and an alkaline earth hydroxide is described in U.S. Pat. No. 4,021,522. The collagen-protein dispersion produced by prior art as exemplified by U.S. Pat. No. 3,634,561, and U.S. Pat. No. 3,894,132, in that when dispersion according to the method of U.S. Pat. No. 4,021,522 was tested for extractability by the process described in U.S. Pat. No. 3,634,561, the extractability was so low as to by unmeasurable, i.e. less than 0.1% by weight. The disclosed extracted collagen-proteins retain the telopeptides on the ends of the protein molecules consistent with the absence of proteolytic enzyme usage in the preparation of a collagen-dispersion using methods described in U.S. Pat. Nos. 3,634,561 and 4,021,522.

SUMMARY OF THE INVENTION

Jellyfish proteins consist almost entirely of proteins rich in glycine and proline and approximate a form of tissue generally referred to as collagen. Collagens obtained from various species are generally unique to the organism from which they are derived and/or to the type of tissue in the organism(s) from which they are derived. Analysis of the amino acid composition of mesogloea hydrolysate show that glycine is the most abundant amino acid, and that hydroxyproline and hydroxylysine, which are characteristic of collagen, are present. Tryptophan is almost totally absent. Thus, mesogloea contain proteins belonging to the collagen group of proteins.. The collagen fibers are associated with mucopolysaccharides and the whole tissue has the character of an organic hydrophilic colloid. Of the total tissue protein in the mesogloea, approximately 80 to 90% is estimated to be collagen, rich in hydroxylysine and its glycosides.

Fresh jellyfish contain approximately 95 to 98% water by weight, depending on the particular species and approximately 2 to 3% salt by weight, which is in approximate osmotic equilibrium with salt water. The contents of solids other than salt is extremely low; not much higher than 1% by weight. Protein content is approximately 1.3%. The lipid content of jellyfish is very low. On a wet-weight basis, lipid contents in the range 0.0046 to 0.2% have been reported. The nonpolar lipids of lyophilized jellyfish comprised 31.1% of the total lipids and sterols may account for approximately 47.8% of the nonpolar lipids. The cholesterol content of four species of coelenterates was in the range of 72.2 to 88.8% of the sterol content. Calculated from the above values, the cholesterol content on a wet-weight basis would be less than 0.35 mg/100 gm. Commercially available processed jellyfish contains approximately 5.5% protein, 25% salt and 68% water, however this type of jellyfish would be for consumption and would need to be alesalted prior to consumption. As a food-stuff, the protein content of jellyfish in terms of protein level is similar to foods such as pasta and boiled rice.

The present invention is concerned with the preparation of collagen from invertebrate species including invertebrate species of marine-jellyfish which constitutes several hundreds of species of primitive marine animals belonging to the class Scyphozoa, phylum Coelenterata. However, the present invention is not restricted to this class of marine organisms and the invention is included by reference to other species of invertebrates present in the marine environment where collagen might be expected to possess similar physical and chemical characteristics that might render similar collagen preparations when the present invention is applied in the extraction and preparation Of collagen dispersions. The fibrous invertebrate type V collagen products formed in the present invention are unique from previous collagen products formed from vertebrate animals species in that the marine jellyfish live and function in an environment different from that in which the vertebrate animal species live and function. The marine jellyfish are found in saltwater environments hypertonic to vertebrate animals; are poikilothermal, i.e. have a body temperature that varies with the environmental temperature, and generally live and function at low temperatures compared to the body temperatures of most vertebrate species; live under variable pH conditions, but generally at pH values significantly less than "physiological" pH (pH 7.4) characteristic of vertebrate species; and lack significant tensile strength in their body structures. These attributes, i.e. pH, temperature, salt concentration, and tensile properties, represent important parameters used in the extraction and preparation of collagens from vertebrate species and thus, extraction and preparation of collagens from marine jellyfish would constitute a unique and novel process and the resultant invertebrate type V collagen preparation has unique and novel properties compared to collagen preparations from vertebrate species.

In the present invention, marine jellyfish of various genera, are subjected to mild mechanical disruption followed by mild acid solubilization of the disrupted tissue. Collagens are precipitated by salts with mild shearing and/or by continuous dialysis and are formed into aqueous, gelled, precipitated, and/or mat/sponge preparations. The fibrous collagen preparation(s), are useful in a variety of medical, dental, and/or nutritional applications (Kimura, S., et al., *J. Food Sci.* 48:1758–1760 (1983)) depending on the purity of the collagen preparation and/or heterogeneity of jellyfish components allowed to remain in the preparations. The fibrous aggregates may be used directly for a variety of purposes or may be chemically or physically cross-linked to provide fibers having substantial structural integrity and macroscopic dimensions. Depending on the intended use of the fibrous materials, the fibers and/or other resident natural components may be treated in a variety of ways to prepare various articles of manufacture.

DESCRIPTION OF THE SPECIFIC EMBODIMENTS

A method is provided for preparation of commercially useful amounts of invertebrate type V collagen from marine jellyfish which may be formed into a variety of formulations and/or products. The collagen is most conveniently prepared from the whole organism, but the hemispherical bell-shaped transparent umbrella may be separated from the numerous fine marginal tentacles and reproductive and/or digestive structures present in the umbrella may be removed and the partial umbrella used in the production of various collagen preparations. Depending on the intended use of the derived fibrous materials, the native collagen may be freed of extraneous matter such as lipids, saccharides, and noncollagenous proteins so as to leave a more pure collagen. Another approach might include a preparation where the intended use of the fibrous materials included consumption of the product as a food-stuff and in this application of the present invention, the native collagen may be less extensively purified such that the foregoing nutritionally important components of the jellyfish are retained in the product(s).

The nonhelical terminal portions of the native collagen-protein molecule, the telopeptides, extend as random coils from the amino and carboxyl ends of the molecules and may be retained or enzymatically removed in preparation of the final product(s). The telopeptides appear to serve a number of functions in the formation of the native collagen fiber. The telopeptides serve as the primary sites for cross-linking intramolecularly (between the three constituent polypeptide chains in the native collagen molecule) and intermolecularly (between two or more native collagen molecules).

In accordance with one attribute of the present invention, invertebrate type V collagen is produced essentially free of noncollagenous proteins and other substances naturally present in marine jellyfish. This collagen is soluble in dilute aqueous acid, including for example dilute organic or inorganic acid including for example, 0.01M acetic acid, and 0.001N HCl. Any insoluble collagen, if present, may be removed by filtration, centrifugation, or other means known to those of ordinary skill in the art.

In accordance with a second attribute of the present invention, invertebrate type V collagen is produced which retains appropriate noncollagenous proteins and/or polysaccharides naturally present in marine jellyfish. This collagen preparation is soluble in dilute aqueous acids including dilute organic and inorganic acids. Nonsoluble components and or tissue structures may be removed by filtration, centrifugation, or other means.

Once the collagen solution is obtained, it may be employed for preparing fibrous aqueous solutions, fibrous aqueous gels, fibrous freeze-dried mats/sponges, and/or highly cross-linked aqueous or freeze-dried products. The procedure for preparing the fibrous preparations involves a slow precipitation of the collagen from solution while subjecting the aqueous medium to mild shear (stirring). The temperatures employed generally range from 0° C. to 42° C., more usually from 10° C. to 30° C., and preferably from 15° C. to 25° C. The pH is generally in the range of about 3 to 9, more usually in the range of 5 to 8, and preferably between 6 and 7.52 A wide variety of salts may be used, preferably alkali metal salts, both neutral and alkaline, more preferably sodium and potassium, with mono and polyvalent cation salts, particularly halides, e.g. chloride. The concentration of the salt may vary widely with the other conditions employed, e.g. temperature, and protein concentration, as well as the particular salt employed. Applicable concentrations generally range from about 0.05M to 4.0M, preferably 1.0M to 3.8M, and, more preferably between 2.5M and 3.5M. Applicable concentrations of polyvalent salts include from about 0.5M to 4.0M, with more appropriate concentrations ranging from 1.0M to 4.0M and the most preferred concentrations ranging from 2.5M to 4.0M. The concentration of collagen in the solutions being precipitated may range between 0.01 mg/ml and 10 mg/ml, with the more preferred concentration range being 0.1 mg/ml to 5 mg/ml, and the most preferred concentration range being between 0.5 mg/ml and 4 mg/ml. Times in which the precipitation will occur will vary from about 10 minutes to 5 hours, preferably about 30 minutes to 2 hours, and most preferably about 1 hour to 1.5 hours.

Various techniques may be used to obtain the desired rate of precipitation of collagen while applying the mild shearing. One technique is heat gelation, wherein a constant or slowly increasing temperature is employed to bring about precipitation of collagen in the presence of salt. Generally, the temperature range is from about 4° C. to 45° C., the temperature being slowly raised from about 4° C. to 10° C. to a temperature of about 20° C. to 37° C. Salt concentrations generally vary from about 1.0M to 4.0M. Alkali metal halides, e.g. sodium chloride, are preferably employed. The pH is generally from 4.0 to 8.0, preferably 5.0 to 6.0. Particularly preferred conditions are nonphysiological conditions for the jellyfish, namely 3.5M NaCl, pH 5.0, with a final temperature of about 35° C.

A second technique to obtain a desired rate of precipitation is to provide a slow increase in ionic strength, pH, and temperature with the collagen in solution. This can be achieved by employing dialysis with a monovalent or polyvalent salt dialysate, thereby slowly raising the salt concentration (or ionic strength) while the acid in the collagen solution diffuses from the collagen solution into the dialysate. The change in pH can be either continual or incremental, preferably by employing alkali salts in the dialysate. Usually the dialysate has a salt concentration of 1.0M to 4.0M, more preferably to 2.5M to 3.8M, particularly of disodium phosphate. The final pH of the medium is generally 3.0 to 8.5, preferably 4.0 to 6.5, and most preferably 5.0 to 5.5.

Another precipitation procedure is that of continuous dialysis at moderately reduced to low temperatures while changing the dialysate from a dilute mildly acidic solution (generally a mild mono or dicarboxylic organic acid or dilute mineral acid such as HCl) to a mildly basic salt solution, while increasing the ionic strength or salt concentration by using a dialysate of increasing salt concentration. With increasing ionic strength or salt concentration, the temperature of the solution may also be increased, until a fibrous mass is obtained. The fibrous mass is freed of any nonfibrous materials and may be treated in a variety of ways depending on the intended use.

Fibrous materials may be used in a wide variety of medical and dental applications as gels, films, sponges, bags, tubes, laminates threads, fibers and specialized three-dimensional structures for unique physical and biological applications, for example microcarrier beads and/or matrices for mammalian cell culture. Fibrous collagen may be used as implants, e.g. packing in combination with collagen from other sources as emulsions, prosthetic devices, and the like.

In describing the present invention, three stages will be considered. The first stage is the purification of native collagen and its transformation into collagen in solution. The second stage is the transformation of the collagen in solution into native fibrous polymers. The third stage is the use of the fibrous polymers with or without cross-linking, for the fabrication of various articles or the formation of composites. Methods for physically or chemically cross-linking are known and may be readily selected and employed by one of ordinary skill in the art to which the present invention pertains.

Collagen in Solution

Collagen can be obtained from a wide variety of Coelenterata. Collagen dispersions obtained from the mantle, tenticles, and whole organism may be expected to provide similar collagen dispersions. The initial stage is to clean the organism of reproductive and digestive tissue structures and tentitles. The mantle portion of the jellyfish typically provides the most uniform materials for production of collagen dispersions with the least amount of noncollagenous protein material(s).

To enhance the ease of purification and facilitate solubilization of collagens, the material is subjected to various mechanical treatments such as dissection, grinding, high speed shearing. Depending on the particular treatment; the tissue may be wet or dry, frozen or cooled, high speed shearing preferably being frozen or cooled wet, and grinding preferably being dry cooled.

Coarsely divided tissues are swollen in aqueous acidic solutions under nondenaturing conditions. Further dispersion is achieved using high speed shearing in short bursts. Preferably dilute acid solutions at low temperatures are employed to minimize denaturation. Suitable acids are acetic, malonic, or lactic acids, or other lyotropic carboxylic acids having pH values from about 2 to 5 at room temperature. Dilute mineral acids such as HCl may also be used provided the pH of the dilute acid solution is approximately 2 to 5. Concentrations of the organic acid in the dispersion medium typically range from about 0.01M to 1.0M and the temperature may vary from 4° C. to about 25° C. Preferably, 0.5M acetic acid solubilization for 2–3 days yields a collagen dispersion which may be filtered through cheesecloth. The acid soluble extract may be dialyzed against sodium phosphate buffer and the formed precipitate redissolved in 0.5M acetic acid. Solid NaCl may be slowly added to the acid solubilized preparation to a final concentration of about 3.5M to effect secondary precipitation. Precipitated collagen dispersion may be redissolved in dilute acid and freeze-dried.

Preparation of atelopeptide collagen dispersion may be accomplished by solubilizing collagen or dissolving the freeze-dried collagen preparation in dilute acid and digesting the materials with 4–10%, weight per weight, pepsin, ficin, or other suitable proteolytic enzyme at temperatures between 4° C. and 37° C. After 24 hours, the digest may be dialyzed against sodium phosphate and precipitated by addition of solid NaCl. The formed precipitate may be redissolved in dilute acid and freeze-dried.

In the present invention, a preferred embodiment is to utilize as a source of collagen, mantle from jellyfish whereby the collagen-containing material is separated from adjacent tissues by dissection, cut into small pieces, soaked in dilute acid at room temperature, and ground using short bursts of high speed shear as in a blender. This technique is found to provide a homogeneous dispersion of jellyfish which is readily available to subsequent chemical and/or enzymatic treatment, so as to provide an efficient means for achieving collagen in solution.

The dispersion which is obtained by treatment with acid is a viscous dispersion containing native fibrillary collagen and a small amount of native collagen in solution.

The viscous product, which may now be referred to as dispersed swollen collagen, consists essentially of a invertebrate type-V collagen of the composition alpha1alpha2alpha3. Enzymatic treatment may be used to remove telopeptides producing atelopeptide fibrillar collagen while leaving the major portion of the molecule intact. Illustrative enzymes include pepsin, ticin, trypsin, pronase, etc. See U.S. Pat. Nos. 3,131,130 and 3,530,037 for similar treatment of vertebrate collagens..

Depending on the particular enzyme employed, the conditions for the enzymatic cleavage of the telopeptides will vary. With pepsin an acidic solution is employed, generally at a pH of about 2 to 4. The concentration of the enzyme varies from about 0.001 to 10 weight percent based on the weight of collagen present. The collagen concentration generally varies from 0.5 g/l to 10 g/l, more usually from about 1 g/l to 5 g/l.

Preferably, the acidity is provided by an organic acid such as a carboxylic acid in a concentration of about 0.01M to 1.0M, and most preferably from 0.1 to 0.8M acetic acid. If necessary, the pH can be adjusted by the addition of a mineral acid, e.g. hydrochloric.

The solution of soluble fibrillar collagen is then treated to separate the soluble fibrillary collagen from soluble noncollagenous materials. Primarily, the treatment involves separations, precipitations, and dialysis against various solutions of different ionic strength. Moderate temperatures are employed, normally between 0° C. and 20° C., and salt solutions of varying ionic strength and salt concentration, generally from about 0.01M to 4.0M. depending on the particular salt.

Neutral salt solutions, e.g. NaCl, of about 0.5M to 4.0M may be employed as a dialysate in a free-flow dialysis at a pH of at least 5 and not greater than about 9. Non-soluble contaminants which have been precipitated during preparation of soluble fibrillar collagen are filtered off to yield a filtrate which contains collagen in solution.

The collagen in solution is precipitated as a part of a purification scheme, for example by adding a neutral salt to the solution to a concentration of about 1.0M to 4.0M, more preferably 3.3 to 3.7M. Various alkali metal halides, e.g. NaCl, may be used. The resulting precipitate is isolated, for example by centrifugation. Further treatment includes exchanging with a dilute carboxylic acid, e.g. acetic acid (0.05M to 0.5 M) in the presence of aqueous NaCl (0.001 to 0.1 weight percent) with precipitation by addition of NaCl (1 to 4M) and resolubilization to insure the purity of the collagen.

Specifically, the procedure may involve an initial precipitation by use of a neutral salt (at least 10 to 30 weight percent), isolation of the precipitate, redissolving in dilute acid, e.g. a carboxylic acid of about 0.05M to 1.0M, filtration, precipitation of the collagen with about 2 to 10 weight percent aqueous salt solution, isolation, redissolution with a dilute carboxylic acid, with repetition of the purification process until the desired degree of purity. The collagen is then resuspended in dilute acid solution, preferably a carboxylic acid such as acetic acid at a concentration of bout 0.01M to 0.5M.

Precipitation of the collagen can be achieved in a variety of ways, including by the addition of neutral salt. Preferably, mild conditions are employed to prevent denaturation and disruption of the natural fibrillar character of collagen. The collagen dispersion may now be concentrated, for example by dialysis, to a concentration of about 1 mg/ml to 20 mg/ml. The clear solution of collagen is relatively free of higher aggregates, is viscous, and consists essentially of fibrillar invertebrate type V collagen.

The non-cross-linked or cross-linked fibrillar collagen is useful in a variety of products including for example as a binder, emulsifying agent, in for example pharmaceutical products, cosmetics, as a foodstuffs, and as medical products including for example, sterile surgical sponges. The present collagen may be used directly as a gel. As a gel, the fibrillar collagen can be used as a vitreous body. The fibrillar collagen can be cast into various forms at varying collagen fiber density and cross-linked to form mat or sponge-like structures which may be used in a variety of applications such as wound dressing, biomaterials for construct of bioprosthetic devices, carriers of other biological compounds such as antibiotics, growth factors, protein factors, bandage, tissue culture materials; or as food-stuff, including but not limited to binders, additives, casings, distinct from foodstuffs and products provided in the form of salted or whole/pans jellyfish. Articles of matter produced using invertebrate marine fibrillar, collagen may be expected to be different from similar articles of matter produced using collagen preparations obtained from vertebrate species.

The following examples are offered by way of illustration, not by the way of limitation.

EXAMPLES

Example 1:. Preparation of Porous Invertebrate Type V Collagen Sheets (Sponges)

In this example, cannon-ball jellyfish were dissected to separate the mantle from the tenticles and the reproductive and digestive organ was dissected from the mantle. The mantle was then cut into small pieces and placed into dilute acetic acid such that approximately 10 mantles of average sized jellyfish (8 to 12 inches in diameter) were placed into 4 liters of 0.5M acetic acid in distilled water. The container was covered to restrict evaporation and placed under refrigeration between 4° C. and 10° C. for three days. The viscous collagen solution was filtered through 4 layers of cheesecloth and the viscous materials precipitated by the addition of solid sodium chloride to a final concentration of 3.5M. The sodium chloride was added in small increments and the precipitated materials removed as formed by the salt precipitation. Essentially all of the collagen was thus precipitated by the addition of sodium chloride and transferred into a separate container. The precipitated collagen was then gently and quickly washed with distilled water to remove associated salt crystals and then 2 liters of 0.5M acetic acid was added to resolubilize the precipitated collagen. This resolubilized material was freeze-dried. The freeze-dried material was then removed from the container and dispersed into small fragments using short bursts of a waring-blender. The resultant dried collagen may be stored until used in the preparation of a desired product. In this example, the dried collagen was rehydrated in distilled water, pH 4.5 to 5.5, at 4° C. to 10° C. and quickly cast into a shallow-pan, casting tray, of known dimensions such that a layer 1 cm thick was obtained. This preparation was allowed to gel at room temperature and was then refrozen by placing the tray into a freezer at −20° C. to −50° C. The frozen gel was freeze-dried to a residual moisture level below 5%, at which time it was removed from the casting tray and cut into porous collagen sheets (sponges).

Example 2: Preparatio of Porous Invertebrate Type V Collagen Sheets (Sponges)

In this example, cannon-ball jellyfish were dissected to separate the mantle from the tenticles and the tenticles were cut into small pieces. These small pieces were then placed into dilute acetic acid such that the tentitles from approximately 10 average sized jellyfish (8 to 12 inches in diameter) were placed into 4 liters of 0.5M acetic acid in distilled water. The container was covered to restrict evaporation and placed under refrigeration between 4° C. and 10° C. for three days. The viscous collagen solution was then filtered through 4 layers of cheese-cloth and the viscous materials precipitated by the addition of solid sodium chloride to a final concentration of 3.5M. The sodium chloride was added in small increments and the precipitated materials were removed as formed and transferred in a separate container. The precipitated collagen was gently and quickly washed with distilled water to remove associated salt crystals and then 2 liters of 0.5M acetic acid were added to resolubilize the precipitated collagen. This resolubilized collagen was frozen as a thin layer to maximize the surface area to volume ratio and freeze-dried. After freeze-drying, the resultant material was removed from the container and dispersed into small fragments using short bursts of a waring-blender. This dried collagen was rehydrated in distilled water, pH 4.5 to 5.5, at 4° C. to 10° C. and quickly cast into a shallow pan, casting tray, of known dimensions such that a layer 2 cm thick was obtained. This preparation was allowed to gel at room temperature and is then refrozen by placing the tray into a freezer at −20° C. to −50° C. The frozen gel was freeze-dried to a residual moisture level below 5 %, at which time it was removed from the casting tray and cut into the desired size of porous invertebrate type V collagen sheets (sponges).

Example 3: Preparation of Porous Invertebrate Type V Collagen Cylinders (Sponges)

In this example, cannon-ball jellyfish were dissected to separate the mantle from the tenticles and the reproductive and digestive organs dissected from the mantle. The mantle and the tenticles were then cut into small pieces and placed into dilute acetic acid such that approximately mantles and tentitles of 10 average sized jellyfish (8 to 12 inches in diameter) were placed into 6 to 8 liters of 0.5M acetic acid in distilled water. The container was covered to restrict evaporation and placed under refrigeration between 4° C. and 10° C. for two to four days. The viscous collagen solution was filtered through 4 layers of cheese-cloth and the viscous materials precipitated by transfer into dialysis bags and dialyzed again 4M sodium chloride to 1 a final salt concentration of 3.5M. Essentially all of the collagen was thus precipitated by the addition of sodium chloride and transferred into a separate container from the dialysis bags. The precipitated collagen was redissolved in 2 liters of 0.5 acetic acid. This resolubilized collagen was frozen as a thin layer to maximize the surface area to volume ratio and freeze-dried. After freeze-drying, the resultant material was removed from the container and dispersed into small fragments using short bursts of a waring-blender. This dried collagen may be stored until used in the preparation of a desired product. In this example, the dried collagen (0.5 gm/100 mls water) was rehydrated in distilled water, pH 4.5 to 5.5, at 4° C. to 10° C. and quickly cast into a hollow tube of known dimensions such that a cylinder of approximately 1 cm in diameter is obtained. This preparation was allowed to gel at room temperature and the gels were extruded from the casting tubes and then refrozen by placing the collagen cylinders into a freezer in an appropriate container at −20° C. to −50° C. The frozen gels were freeze-dried to a residual moisture level below 5%, at which time they were removed from the container and cut into the desired size of porous collagen cylinders (sponges).

Example 4: Preparation of Invertebrate Type V Collagen Solution

In this example, cannon-ball jellyfish were dissected to separate the mantle from the tenticles and the reproductive and digestive organs were dissected from the mantle. The mantle was then cut into small pieces and placed into dilute acetic acid such that approximately 10 mantles of average sized jellyfish (8 to 12 inches in diameter) were placed into liters of 0.05 N hydrochloric acid in distilled water. The container was covered to restrict evaporation and placed under refrigeration between 4° C. and 10° C. for three days. The viscous collagen solution was filtered through 4 layers of cheese-cloth and the viscous materials precipitated by the addition of solid sodium chloride to a final concentration of 3.5M. The sodium chloride was added in small increments and the precipitated material removed as formed by the salt precipitation. Essentially all of the collagen was thus precipitated by the addition of sodium chloride and was then transferred into a separate container. The precipitated collagen was gently and quickly washed with distilled water to remove associated salt crystals and then 2 liters of 0.05-N hydrochloric acid were added to resolubilize the precipitated collagen. This resolubilized collagen was frozen as a thin layer to maximize the surface area to volume ratio and freeze-dried. After freeze-drying the material was removed from the container and dispersed into small fragments using short bursts of a waring-blender. The dried collagen was sorted until used in the preparation of a desired product. In this example, the dried collagen was rehydrated in isotonic phosphate buffered saline, pH 3.0 to 4.0, at 4° C. to 10° C., and provided as a viscous invertebrate type V collagen solution.

Example 5: Preparation of Cross-Linked Invertebrate Type Collagen Sheets (Sponges)

In this example, cannon-ball jellyfish are dissected to separate the mantle from the tenticles and the reproductive and digestive organs are dissected from the mantle. The mantle is then cut into small pieces and placed into dilute acetic acid such that approximately 10 mantles of average sized jellyfish (8 to 12 inches in diameter) are placed into 4 liters of 0.5M acetic acid in distilled water. The container is covered to restrict evaporation and placed under refrigeration between 4° C. and 10° C. for three days. The viscous collagen solution is then filtered through 4 layers of cheese-cloth and the viscous materials precipitated by the addition of solid sodium chloride to a final concentration of 3.5M. The sodium chloride is added in small increments and the precipitated materials are removed as formed by the salt precipitation. Essentially all of the collagen is thus precipitated by the addition of sodium chloride and is transferred into a separate container. The precipitated collagen is gently and quickly washed with distilled water to remove associated salt crystals and then 2 liters of 0.5M acetic acid is added to resolubilize the precipitated collagen. This resolubilized material is freeze-dried. The freeze-dried material is then removed from the container and dispersed into small fragments using short bursts of a waring-blender. The resultant dried collagen may be stored until used in the preparation of a desired product. In this example, the dried collagen is rehydrated in distilled water, pH 4.5 to 5.5, at 4° C. to 10° C. and quickly cast into a shallow pan, casting tray, of known dimensions such that a layer 1 cm thick is obtained. This preparation is allowed to gel at room temperature. This wet mixture is then soaked in a cross-linking reagent solution containing preferably 0.001% to 0.005% glutaraldehyde or formaldehyde or both, for about 20 to 30 hours, preferably about 24 hours at room temperature. The cross-linked gel is then washed and refrozen by placing the tray into a freezer at −20° C. to −50° C. The frozen gel is freeze-dried to a residual moisture level below 5%, at which time it may be removed from the casting tray and cut into the desired size of porous collagen sheets (sponges).

All of the publications cited herein are to be incorporated by reference into the parent disclosure. It will be appreciated by those skilled in the art that various modifications can be made without departing from the essential nature thereof. It is intended to encompass all such indications within the scope of the appended claims.

What is claimed:

1. Substantially pure invertebrate type V telopeptide collagen isolated from one or more species belonging to the class Scyphozoa in the Coelenterata.

2. The invertebrate type V telopeptide collagen of claim 1, wherein said collagen is cross-linked.

3. The invertebrate type V telopeptide collagen of claim 1, wherein said species comprise one or more species of jellyfish.

4. The invertebrate type V collagen of claim 3, wherein said jellyfish comprise one or more elements selected from the group consisting of the mantle, tenticles and the whole organism.

5. The invertebrate type V telopeptide collagen of claim 1, wherein said collagen comprises 0.25 to 95 wt % of collagen-protein.

6. The invertebrate type V telopeptide collagen of claim 1, produced by the process comprising:

extracting said invertebrate type V telopeptide collagen from one or more invertebrate species in dilute acid to form extracted telopeptide collagen, and precipitating said extracted telopeptide collagen from said dilute acid to form precipitated telopeptide collage.

7. The invertebrate type V telopeptide collagen of claim 6, wherein said step of precipitating is performed using a salt solution.

8. The invertebrate type V telopeptide collagen of claim 6, wherein said salt solution has a salt concentration of from 0.1M to 4.0M.

9. The invertebrate type V telopeptide collagen of claim 6, wherein said salt solution comprises one or more alkali metal halides.

10. The invertebrate type V telopeptide collagen of claim 6, wherein said process further comprises:

resolubilizing said precipitated telopeptide collagen to form resolubilized collagen telopeptide , and freeze-drying said resolubilized telopeptide collagen.

11. The invertebrate type V telopeptide collagen of claim 10, wherein said process further comprises cross-linking said resolubilized telopeptide collagen prior to freeze-drying.

12. The invertebrate type V telopeptide collagen of claim 6, wherein said dilute acid comprise one or more members selected from the group consisting of dilute organic acid and dilute inorganic acid.

13. The invertebrate type V telopeptide collagen of claim 12, wherein said organic acid comprises one or more members selected from the group consisting of acetic acid, lactic acid, malic acid, citric acid, glutaric acid, and propionic acid; and said inorganic acid comprises hydrochloric acid.

14. A method for producing substantially pure invertebrate type V telopeptide collagen from one or more species of jellyfish, comprising the steps of extracting telopeptide collagen from said one or more species of jellyfish to form extracted telopeptide collagen; and precipitating said extracted telopeptide collagen from said dilute acid with a salt solution to form precipitated telopeptide collagen.

15. The method of claim 14, further comprising the steps of resolubilizing said precipitated telopeptide collagen to form resolubilized telopeptide collagen; and freeze-drying said resolubilized telopeptide collagen to form freeze-dried invertebrate type V telopeptide collagen.

16. The method of claim 15, further comprising the step of cross-linking said resolubilized collagen prior to freeze-drying.

* * * * *